United States Patent [19]

Koermer

[11] 4,006,190
[45] Feb. 1, 1977

[54] PRODUCTION OF HYDROXYL COMPOUNDS

[75] Inventor: Gerald S. Koermer, Corpus Christi, Tex.

[73] Assignee: Celanese Corporation, New York, N.Y.

[22] Filed: Mar. 15, 1976

[21] Appl. No.: 666,842

[52] U.S. Cl. .................................. 260/602; 203/74; 260/75 R; 260/247.7 Z; 260/326.8; 260/581 R; 260/584 R; 260/577; 260/635 A; 260/635 R; 260/637 R
[51] Int. Cl.[2] ................. C07C 47/19; C07C 29/14; C07C 31/20
[58] Field of Search ....................... 260/635 A, 602

[56] References Cited

UNITED STATES PATENTS

| | | | |
|---|---|---|---|
| 2,808,440 | 10/1957 | Dickey et al. | 260/635 A |
| 2,975,218 | 3/1961 | Buchner et al. | 260/635 A |
| 3,365,481 | 1/1968 | Wittig et al. | 260/602 |
| 3,852,360 | 12/1974 | Vilkas et al. | 260/602 |

Primary Examiner—Joseph E. Evans
Attorney, Agent, or Firm—Stewart N. Rice

[57] ABSTRACT

A sterically hindered enamine (vinyl amine) is reacted with an alkylene oxide followed by hydrolysis of the reaction product to produce a monohydroxyl alkyl aldehyde wherein the hydroxyl group is on the third carbon atom from the carbonyl group, such as 4-hydroxybutanal. The monohydroxyl alkyl aldehyde may be further hydrogenated to produce the corresponding alkanediol, such as 1,4-butanediol.

14 Claims, No Drawings

PRODUCTION OF HYDROXYL COMPOUNDS

BACKGROUND OF THE INVENTION

Alkanediols, such as 1,4-butanediol are valuable and desirable products in the chemical industry as they find a variety of uses. Probably the most valuable use of these compounds is as a raw material for the formation of copolymers such as polyesters. In view of the industrial importance of these alkanediols, research is constantly underway for new methods of producing them from readily available starting materials.

One known method of producing an alkanediol is by the reduction of a monohydroxyl alkane aldehyde. For example, 4-hydroxybutanal may be reduced by hydrogenation to 1,4-butanediol. Other methods include the Reppe method wherein acetylene is reacted with formaldehyde to produce an unsaturated diol which is then reduced to the alkanediol. At the present time alkanediols are not produced in commercial quantities from monohydroxyl alkyl aldehydes because these latter products themselves are not readily available in sufficient quantities and at low enough prices to justify such means of commerical production. New methods of producing the monohydroxyl alkane aldehydes are thus desired.

It is thus an object of the present invention to provide a new process for the production of alkanediols, more specifically those wherein the two hydroxyl groups thereof are separated by four carbon atoms. It is a particular object of the present invention to provide a process for the production of 1,4-butanediol. It is an additional object of the present invention to provide a process for the production of a monohydroxyl alkyl aldehydes, more specifically those wherein the hydroxyl group thereof is on the third carbon atom from the carbonyl group thereof. It is another object of the present invention to produce aqueous solutions of such monohydroxyl alkyl aldehydes. Another and further particular object of the present invention is to produce 4-hydroxybutanal and aqueous solutions thereof. Additional objects will become apparent from the following description of the present invention.

SUMMARY

The foregoing and additional objects are accomplished by the present invention which in one of its aspects is a process comprising the successive steps of: (a) reacting in a liquid phase a sterically hindered enamine with an alkylene oxide, said sterically hindered enamine being of the formula

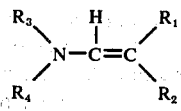

wherein $R_1$ and $R_2$ are alike or different and are hydrogen or lower alkyl groups, and wherein $R_3$ and $R_4$ are each an organic group containing at least three carbon atoms or which compositely form a single divalent organic group containing at least six carbon atoms, $R_3$ and $R_4$ being of a nature to sterically hinder the nitrogen atom of said enamine but which contain no groups which under process conditions are reactive to any substantial extent with themseleves, with said enamine or with the other reactants used and products formed in this said process, said alkylene oxide being of a formula

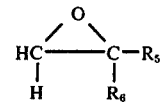

wherein $R_5$ and $R_6$ are alike or different and are hydrogen or lower alkyl groups, (b) hydrolyzing the compound formed by the reaction of said enamine with said alkylene oxide by combining therewith under hydrolysis condition a stoichiometric excess of the amount of water necessary for the hydrolysis of said compound to produce a two-phase hydrolysis reaction product consisting of an oil phase rich in a sterically hindered secondary amine and an aqueous phase comprising an aqueous solution of a monohydroxyl alkyl aldehyde of the formula

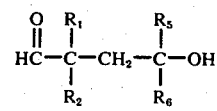

wherein $R_1$, $R_2$, $R_5$ and $R_6$ are set forth above, and (c) treating said two-phase hydrolysis reaction product to separate and recover therefrom said aqueous phase comprising an aqueous solution of a said monohydroxyl alkyl aldehyde. Another aspect of the present invention comprises the additional step of recovering a monohydroxyl alkyl aldehyde from the said aqueous solution thereof. In still another aspect the present invention comprises the hydrogenation of said aqueous solution so as to convert the aldehyde to an alkanediol.

DETAILED DESCRIPTION OF THE INVENTION

The first step in the present invention involves the reaction of a sterically hindered enamine with an alkylene oxide. Enamines are also known as vinyl amines and those useful in the present invention are of Formula I as set forth above. The nitrogen atom of the enamine must be sterically hindered to direct reactivity of the enamine away from the nitrogen atom to the second carbon removed therefrom which is adjacent to the ethylenic unsaturation, that is to the carbon atom to which $R_1$ and $R_2$ are attached. In order to sterically hinder the nitrogen atom $R_3$ and $R_4$ must be an organic radical of at least three carbon atoms, for example an isobutyl group. Alternatively, $R_3$ and $R_4$ may compositely form a single divalent organic group containing at least six carbon atoms, in which case the nitrogen atom of the enamine becomes a heteroatom in a heterocyclic compound.

Generally speaking, $R_3$ and $R_4$ should each be a non-straight chain organic group, or compositely form a single non-straight chain organic group, free of ethylenic and acetylenic unsaturation adjacent to nitrogen and having no atoms in addition to carbon and hydrogen other than etheral oxygen atoms. Aromatic groups may be present in $R_3$ and $R_4$ but best results are obtained when they are non-aromatic in nature. In order to sterically hinder the nitrogen atom, $R_3$ and $R_4$ should be other than straight-chain in nature. For example, $R_3$ and $R_4$ may each be a non-straight chain radical of the formula

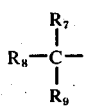

wherein $R_7$ and $R_8$ may be alike or different and are hydrogen or lower alkyl and $R_9$ is an organic radical with the proviso that the $R_9$ of $R_3$ may join with the $R_9$ of $R_4$ such that $R_3$ and $R_4$ compositely form a single divalent non-straight chain organic radical.

Most preferably $R_3$ and $R_4$ are each a branched chain alkyl group of at least three carbon atoms (such as tertiary butyl), preferably 3 to 10 carbon atoms, or which compositely form a branched chain alkylenyl group of at least six, preferably 6 to 15, carbon atoms (such as $-CHCH_3CH_2CH_2CH_3CH-$). By "alkylenyl group" is meant a divalent hydrocarbon radical group free of unsaturation adjacent to nitrogen and of the generic formula $-C_nH_{2n}-$. By lower alkyl is meant an alkyl group of 1 to 6 carbon atoms.

In Formula I above, $R_1$ and $R_2$ may be alike or different and are hydrogen or lower alkyl (preferably 1 to 3 carbons). Since the carbon to which they are attached is to react with an alkylene oxide in the process of the present invention, $R_1$ and $R_2$ taken together should not be of such a size or nature as to sterically hinder such carbon atom. Most preferably both $R_1$ and $R_2$ are hydrogen.

Enamines are well known compounds and those useful in the present invention may readily be formed by reacting a sterically hindered secondary amine of the formula $R_3R_4NH$ with an alkyl aldehyde of the formula $R_1R_2CHCHO$, wherein $R_1$, $R_2$, $R_3$ and $R_4$ are as set forth above, to form an enamine of Formula I above. The reaction between the amine and the aldehyde is a liquid phase reaction which is generally conducted at low temperatures, for example from −20° C to 50° C, and under a pressure sufficient to maintain a liquid phase. When the aldehyde is acetaldehyde, the temperature is preferably −20° C to 0° C. No catalyst is needed in the reaction although a drying agent may usefully be present during the reaction to complex with the water formed in the reaction. Suitable drying agents include potassium carbonate and magnesium sulfate. Alternative to adding a drying agent, an azeotroping agent such as benzene or toluene can be added to aid in the removal of the water. The sterically hindered secondary amine itself will serve as an azeotroping agent if a large excess is used. For a discussion of formation of enamines see British Patent Specification 832,078 published Apr. 6, 1960. Also a lengthy review of enamines is set forth by J. Szmuszkovicz in *Advances In Organic Chemistry*, Vol. 4, 1963, Pgs. 1 et. seq. Suitable sterically hindered secondary amines of the formula $R_3R_4NH$ for reacting with an aldehyde to form an enamine of Formula I above include di-tert-butyl amine, diisopropyl amine, tert-butyl tert-amyl amine, cis 2,5 dimethyl pyrrolidine, 3,5 dimethylmorpholine, diisobutyl amine, isobutyl isopropyl amine, di-neo-pentyl amine and isobutyl neopentyl amine.

The reaction of the enamine with the alkylene oxide is conducted in the liquid phase at temperatures generally within the range of about 10° C to 150° C and preferably within the range of 25° to 120° C. The pressure only needs to be sufficient to maintain the reactants, both the enamine and the alkylene oxide, in the liquid phase and will usually be within the range of atmospheric to ten atmospheres absolute. The necessary pressure will generally depend on the particular alkylene oxide being utilized, ethylene oxide for example having a boiling point of about 13.5° C at atmospheric pressure.

All that is required to effect the reaction between the enamine and the alkylene oxide is to bring them together and intimately contact them under the above mentioned conditions. Gentle agitation during a reaction is recommended. The mole ratio of alkylene oxide to enamine passed to the reaction zone should be at least 0.5/1 although it is preferred that the alkylene oxide/enamine molar ratio be at least 1/1 and more preferably that the alkylene oxide be in excess. Generally speaking, the molar ratio of alkylene oxide to enamine will be within the range of about 0.5/1 to 20/1, preferably 5/1 to 15/1.

No catalyst or promoter is necessary although it is foreseeable that future research might lead to a catalyst or promoter which would enhance the reaction. Thus the use of such a catalyst is not excluded herein. The time allowed for the reaction should generally be at least 2 hours, usually within the range of about 1 to 24 hours. Longer reaction times do not adversely affect the reaction but after about 24 hours probably no substantial increase in conversion will be obtained.

It is theorized that the enamine and the alkylene oxide react to form a compound of the following formula

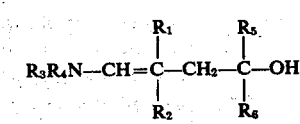

The compound formed may, however, be a heterocyclic compound having a hetero oxygen atom and a $-NR_3R_4$ side group. The inventor does not, however, wish to be held to any particular theory or mechanistic discourse.

The next step of the invention is to hydrolyze the compound formed by the reaction of the enamine with the alkylene oxide, which hydrolysis produces a monohydroxyl alkyl aldehyde of Formula III above wherein the hydroxyl group will be on the third carbon atom from the carbonyl group of the aldehyde. The hydrolysis is accomplished by adding a large excess of the stoichiometric amount of water needed to hydrolyze the compound formed from the enamine-alkylene oxide reaction, stoichiometric amount of water needed being one mole of water per mole of the compound. Preferably an amount of water is used which is at least 5 times such stoichiometric requirement, for example, from 5 to 100 times the stoichiometric requirement and preferably from 10 to 25 times the stoichiometric requirement.

The entire reaction product removed from the enamine-alkylene oxide reaction zone can be passed to hydrolysis or the unreacted alkylene oxide and/or enamine, if any, can be removed therefrom prior to hydrolysis. At least where there are large amounts of unreacted enamine or alkylene oxide present in the reaction product, the removal of such prior to hydrolysis is recommended because of economic reasons. Any alkylene oxide may easily be removed by stripping or flash distillation. Unreacted enamines may be removed by distillation. If the alkylene oxide is not removed prior to hydrolysis, it too will be hydrolyzed by the water, and the amount of water which will be taken up and utilized in hydrolyzing the alkylene oxide must be taken into consideration when determining the total amount of water necessary for hydrolysis of the compound formed by the enamine-alkylene oxide reaction.

Any unreacted enamine which is not removed prior to hydrolysis will decompose to a non-hydroxylated aldehyde and secondary amine.

The hydrolysis can be at atmospheric pressure and ordinary temperatures, e.g., in the range of about 40° C to 100° C. An acidic catalyst, e.g., acetic acid, may be beneficial. In the hydrolysis step water is contacted intimately with the compound formed by reacting the enamine with the alkylene oxide for a hydrolysis reaction time of at least about 45 minutes, preferably at least about one hour. The effect of the hydrolysis reaction step is to break down the compound into a sterically hindered secondary amine of the formula R3R4NH, wherein R3 and R4 are as set forth above, and the monohydroxyl alkyl aldehyde. The hydrolysis will result in a hydrolysis reaction product consisting of two immiscible phases, one being an oil phase and the other an aqueous phase. The oil phase will consist substantially of the sterically hindered secondary amine produced in the hydrolysis and the aqueous phase will comprise an aqueous solution of the monohydroxyl alkyl aldehyde. As pointed out above, any excess enamine present during the hydrolysis will decompose to a secondary amine and a non-hydroxylated aldehyde. This latter aldehyde will usually partition between the oil phase and the aqueous phase while the secondary amine will be in the oil phase.

The aqueous phase and the oil phase readily form two distinct layers through gravity alone since the oil phase is lighter than the aqueous phase. However, the separation may be aided by mechanical means such as the application of centrifugal force in a centrifugal separator. The aqueous phase may be easily separated from the oil phase by a conventional separation technique such as decantation, use of centrifugal separators and the like. The oil phase may be treated by conventional distillation techniques to separate water and other impurities from the sterically hindered secondary amine therein and other impurities from the sterically hindered secondary amine therein and the amine then used to form more of the enamine useful in the invention. The aqueous phase containing the monohydroxyl alkyl aldehyde may be further treated by conventional distillation techniques to recover the aldehyde therefrom; however, the aqueous solution of the aldehyde is in itself a useful commodity since various uses of the aldehyde call for the aldehyde to be diluted prior to use.

In particular, the aqueous solution of the aldehyde finds utility in the production of an alkanediol corresponding to the aldehyde. To be more specific, the aqueous solution of the monohydroxyl alkyl recovered from the hydrolysis may be passed to a hydrogenation zone, either with or without removal of various residual impurities such amines, where the hydrogenation reduces the carbonyl group of the aldehyde to an hydroxyl group so as to produce an alkanediol. The two hydroxyl groups of the alkanediol will be separated by four carbon atoms, the alkanediol produced being of the formula

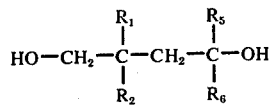  VI wherein $R_1$, $R_2$, $R_5$ and $R_6$ are as set forth above.

The hydrogenation of the monohydroxyl alkyl aldehyde may be advantageously carried out by feeding the aqueous solution thereof together with molecular hydrogen to a hydrogenation zone maintained under hydrogenation conditions while in the presence of a catalytic amount of a hydrogenation catalyst. Suitable temperatures including those within the range of about 10° to 150° C, preferably 25° to 100° C, with suitable pressures being within the range of about 1 to 100 atmospheres absolute, preferably 5 to 50 atmospheres absolute. The hydrogenation catalyst may be substantially any of the known hydrogenation catalysts such as those comprising copper, copper chromite, nickel, cobalt, platinum, or palladium or mixtures thereof. Preferred catalysts are those of palladium or Raney nickel. The catalyst may be unsupported or supported on a conventional support such as carbon or the like.

To accomplish the hydrogenation, the aqueous solution of the aldehyde is contacted with molecular hydrogen while also in contact with the catalyst whereby at least a portion of the hydroxyl alkyl aldehyde will be converted to the alkanediol. The aqueous solution and the hydrogen may be led over a fixed catalyst bed (either a flooded bed or a trickle bed may be used) or the catalyst may be slurried with the aqueous solution and the resulting slurry contacted with the hydrogen. The hydrogen itself may be lead concurrently or countercurrently. As a general rule technically pure hydrogen will be utilized but it is also possible to use gases rich in hydrogen, such as coke oven gas, water gas or town gas.

The hydrogenation should not be so harsh as to adversely affect the hydroxyl group already present on the monohydroxyl alkyl aldehyde. The contact time or residence time will vary widely but will generally be within the range of about 0.5 to 5 hours. The optimum hydrogenation reaction time will, of course, vary widely and will depend on such factors as the rate of hydrogen flow, the temperature, the catalyst, the amount of catalyst, the pressure and other process parameters. In a batch process good conversions may be realized under some conditions after about an hour or less with usual residence times being about 0.5 to 4 hours. In a fixed bed process the flow rate of liquid feed may vary widely, for example, from 100 to 2,000 milliliters per hour per liter of catalyst.

The reactor size of the hydrogenation has no bearing on the operation of the invention but it is presumed that the optimum size to give the proper residence time will be utilized. Reactors of conventional configuration may be used. The size and shape of the catalyst particles are not critical. Thus, the catalyst may be in the form of pellets, powder, saddles, spheres, etc.

Following the hydrogenation the alkanediol produced in the reaction may be recovered by distillation. For example, the product may be passed to an azeotropic distillation tower operated at a reduced pressure of about 0.015 atmospheres absolute so as to remove water; then, if a solvent has been used, to a solvent recovery column operated at reduced pressure; then to an amine stripper column to remove any amines present; then to a heavy ends distillation column operated at reduced pressure to remove any polymers; and then to a finish tower for a final purification.

EXAMPLE I

A vessel containing 14.0 grams of anhydrous potassium carbonate and 0.27 moles of diisobutylamine is cooled to −10° C. To such mixture there is then added, very slowly with stirring, 0.21 moles of freshly distilled cold acetaldehyde. After addition of the acetaldehyde is complete, the reaction mixture is stirred for 3 hours while being maintained at −10° C and then allowed to warm to 0° C. The resulting solution of an enamine is decanted under nitrogen from the solid potassium carbonate. Analysis indicates that about 93% of the acetaldehyde was converted with a selectivity of about 97% to an enamine of Formula I above wherein $R_3$ and $R_4$ are each isobutyl groups and $R_1$ and $R_2$ are hydrogen.

The enamine solution as so obtained is placed in a reactor and there is condensed into such about 1.24 moles of ethylene oxide which is about six times the stoichiometric amount of ethylene oxide necessary to react with the enamine present. The reactor is closed and the reaction mixture heated gently at about 35° C with slow agitation for about 6 hours and then allowed to stand at room temperature an additional 18 hours. The reactor is then opened and the excess ethylene oxide evaporated from the reaction mixture. After the evaporation of the excess ethylene oxide is accomplished, about 36 milliliters of water (about ten times the theoretical amount necessary) is added. The resulting hydrolysis mixture is heated gently at about 60° C with stirring for 24 hours resulting in two phases. The oily upper phase contains mostly secondary amine and amine-containing byproducts while the lower aqueous phase contains mostly water and 4-hydroxybutanal with small amounts of ethylene glycol, the latter resulting from hydrolysis of ethylene oxide not removed by evaporation. Analysis indicates that about 0.03 moles of 4-hydroxybutanal have been produced and are contained in the aqueous solution. The ethylene glycol is removed by distillation to obtain an aqueous solution of b 4-hydroxybutanal containing about 7% by weight of the 4-hydroxybutanal.

EXAMPLE II

An aqueous solution as is obtained according to Example I is continuously extracted with diethyl ether using a continuous extraction apparatus. The resulting ether solution is then placed in an evaporator to evaporate the ether therefrom to obtain a substantially pure 4-hydroxybutanal containing minor amounts of nitrogen-containing impurities.

EXAMPLE III

About 1 liter of an aqueous solution as obtained in Example I is hydrogenated to convert the 4-hydroxybutanal to 1,4-butanediol. The solution is placed in stainless steel rocking autoclave along with 4 grams of Raney nickel hydrogenation catalyst. A hydrogen atmosphere of about 40 atmospheres absolute is applied, the temperature adjusted to 40° C, and the reactor agitated by rocking for 30 minutes after which hydrogen uptake is complete. Analysis indicates substantially complete conversion of the 4-hydroxybutanal to 1,4-butanediol. The 1-4 butanediol is recovered by passing the product from hydrogenation to an azeotropic distillation tower containing 20 sieve trays operated at a reduced absolute pressure of 100 mmHg and 78° C overhead temperature. The aqueous solution along with anisole as an azeotroping agent is passed to the bottom of the tower. Water is removed overhead with the azeotrope while bottoms constitutes 1,4-butanediol and some anisole. The crude 1,4-butanediol containing anisole is then passed to the lower third of a solvent recovery column of 30 trays operated at 45 mmHg absolute pressure and an overhead temperature of 67° C. The anisole is removed as overheads and crude 1,4-butanediol removed as bottoms. The anisole removed overhead also contains most of the amine impurities which were present. The anisole and amine impurities may be separated by distillation if desired.

The crude 1,4-butanediol is then passed to the middle of a heavy ends column (30 trays) operated at 45 mmHg absolute pressure and an overhead temperature of 155° C. Polymer is removed as bottoms and a substantially pure 1,4-butanediol removed as overheads. The substantially pure 1,4-butanediol is further purified in a finishing tower of 30 trays operated at 45 mmHg absolute and an overhead temperature of 115° C, the 1,4-butanediol being removed from the third tray from the bottom.

The embodiments of the invention in which an exclusive property or privilege is claimed are defined as follows:

1. A process comprising the successive steps of:
   a. reacting in a liquid phase a sterically hindered enamine with an alkylene oxide, said sterically hindered enamine being of the formula:

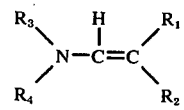

wherein $R_1$ and $R_2$ are alike or different and are hydrogen or lower alkyl groups, and wherein $R_3$ and $R_4$ are each an organic group containing at least three carbon atoms or which compositely form a single divalent organic group containing at least six carbon atoms, $R_3$ and $R_4$ being of a nature to sterically hinder the nitrogen atom of said enamine but which contain no groups which under process conditions are reactive to any substantial extent with themseleves, with said enamine or with the other reactants used and products formed in this said process, said alkylene oxide being of a formula:

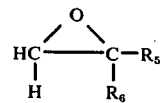

wherein $R_5$ and $R_6$ are alike or different and are hydrogen or lower alkyl groups,
   b. hydrolyzing the compound formed by the reaction of said enamine with said alkylene oxide by combining therewith under hydrolysis condition a stoichiometric excess of the amount of water necessary for the hydrolysis of said compound to produce a two-phase hydrolysis reaction product consisting of an oil phase rich in a sterically hindered secondary amine and an aqueous phase comprising an aqueous solution of a monohydroxyl alkyl aldehyde of the formula:

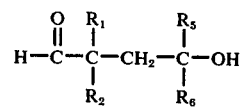

wherein $R_1$, $R_2$, $R_5$ and $R_6$ are set forth above, and c. treating said two-phase hydrolysis reaction product to separate and recover therefrom said aqueous phase comprising an aqueous solution of a said monohydroxyl alkyl aldehyde.

2. The process of claim 1 wherein $R_1$, $R_2$, $R_5$ and $R_6$ are hydrogen.

3. The process of claim 2 wherein $R_3$ and $R_4$ are each an alkyl group of at least three carbon atoms or which compositely form a branched chain alkylenyl group of at least six carbon atoms.

4. The process of claim 3 wherein the said reacting of said enamine with said alkylene oxide is conducted at temperatures within the range of about 10° C to 150° C and wherein the molar ratio of alkylene oxide to enamine is within the range of about 5/1 to 15/1.

5. The process of claim 4 wherein excess alkylene oxide is separated prior to said hydrolyzing.

6. A process comprising the successive steps of:
a. reacting in a liquid phase a sterically hindered enamine with an alkylene oxide, said sterically hindered enamine being of the formula:

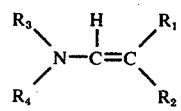

wherein $R_1$ and $R_2$ are alike or different and are hydrogen or lower alkyl groups, and wherein $R_3$ and $R_4$ are each an organic group containing at least three carbon atoms or which compositely form a single divalent organic group containing at least six carbon atoms, $R_3$ and $R_4$ being of a nature to sterically hinder the nitrogen atom of said enamine but which contain no groups which under process conditions are reactive to any substantial extent with themselves, with said enamine or with the other reactants used and products formed in this said process, said alkylene oxide being of a formula:

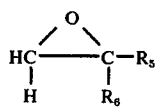

wherein $R_5$ and $R_6$ are alike or different and are hydrogen or lower alkyl groups, b. hydrolyzing the compound formed by the reaction of said enamine with said alkylene oxide by combining therewith under hydrolysis condition a stoichiometric excess of the amount of water necessary for the hydrolysis of said compound to produce a two-phase hydrolysis reaction product consisting of an oil phase rich in a sterically hindered secondary amine and an aqueous phase comprising an aqueous solution of a monohydroxyl alkyl aldehyde of the formula:

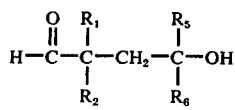

wherein $R_1$, $R_2$, $R_5$ and $R_6$ are set forth above, c. treating said two-phase hydrolysis reaction product to separate and recover therefrom said aqueous phase comprising an aqueous solution of a said monohydroxyl alkyl aldehyde, and d. separating from said aqueous phase a substantially pure monohydroxyl alkyl aldehyde product.

7. The process of claim 6 wherein $R_1$, $R_2$, $R_5$ and $R_6$ are hydrogen.

8. The process of claim 7 wherein $R_3$ and $R_4$ are each an alkyl group of at least three carbon atoms or which compositely form a branched chain alkylenyl group of at least six carbon atoms.

9. The process of claim 8 wherein the said reacting of said enamine with said alkylene oxide is conducted at temperatures within the range of about 10° C to 150° C and wherein the molar ratio of alkylene oxide to enamine is within the range of about 5/1 to 15/1, and wherein the excess alkylene oxide is separated prior to said hydrolyzing.

10. A process comprising the successive steps of:
a. reacting in a liquid phase a sterically hindered enamine with an alkylene oxide, said sterically hindered enamine being of the formula:

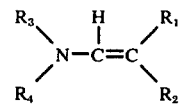

wherein $R_1$ and $R_2$ are alike or different and are hydrogen or lower alkyl groups, and wherein $R_3$ and $R_4$ are each an organic group containing at least three carbon atoms or which compositely form a single divalent organic group containing at least six carbon atoms, $R_3$ and $R_4$ being of a nature to sterically hinder the nitrogen atom of said enamine but which contain no groups which under process conditions are reactive to any substantial extent with themselves, with said enamine or with the other reactants used and products formed in this said process, said alkylene oxide being of a formula:

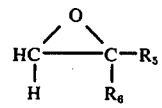

wherein $R_5$ and $R_6$ are alike or different and are hydrogen or lower alkyl groups, b. hydrolyzing the compound formed by the reaction of said enamine with said alkylene oxide by combining therewith under hydrolysis condition a stoichiometric excess of the amount of water necessary for the hydrolysis of said compound to produce a two-phase hydrolysis reaction product consisting of an oil phase rich in a sterically hindered secondary amine and an aqueous phase comprising an aqueous solution of a monohydroxyl alkyl aldehyde of the formula:

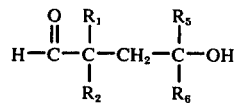

wherein $R_1$, $R_2$, $R_5$ and $R_6$ are set forth above,
c. treating said two-phase hydrolysis reaction product to separate and recover therefrom said aqueous phase comprising an aqueous solution of a said monohydroxyl alkyl aldehyde,
d. contacting said aqueous phase comprising an aqueous solution of a said monohydroxyl alkyl aldehyde with molecular hydrogen under hydrogenation conditions utilizing a catalytic amount of a hydrogenation catalyst whereby at least a portion of the said monohydroxyl alkyl aldehyde contained therein will be converted to an alkanediol of the formula:

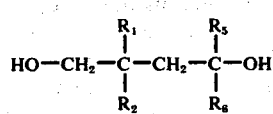

wherein $R_1$, $R_2$, $R_5$ and $R_6$ are as set forth above, and e. recovering a said alkanediol as a product.

11. The process of claim 10 wherein $R_1$, $R_2$, $R_5$ and $R_6$ are hydrogen.

12. The process of claim 11 wherein $R_3$ and $R_4$ are each an alkyl group of at least three carbon atoms or which compositely form a branched chain alkylenyl group of at least six carbon atoms.

13. The process of claim 12 wherein the said reacting of said enamine with said alkylene oxide is conducted at temperatures within the range of about 10° C to 150° C and wherein the molar ratio of alkylene oxide to enamine is within the range of about 5/1 to 15/1, and wherein the excess alkylene oxide is separated prior to said hydrolyzing.

14. The process of claim 13 wherein said hydrogenation is accomplished using a hydrogenating catalyst comprising copper, copper chromite, nickel, cobalt, platinum or palladium or mixtures thereof, and is conducted at temperatures within the range of 25° to 100° C and at pressures within the range of about 5 to 50 atmospheres absolute.

* * * * *